United States Patent [19]
Itoi

[11] Patent Number: 5,837,883
[45] Date of Patent: Nov. 17, 1998

[54] GAS CHROMATOGRAPH/MASS SPECTROMETER

[75] Inventor: Hiroto Itoi, Kita-ku, Japan

[73] Assignee: Shimadzu Corporation, Kyoto, Japan

[21] Appl. No.: 882,290

[22] Filed: Jun. 25, 1997

[30] Foreign Application Priority Data

Jun. 27, 1996 [JP] Japan ................................. 8-188909

[51] Int. Cl.$^6$ .................... G01N 30/02; G01D 11/24; B01D 59/44
[52] U.S. Cl. .................. 73/23.37; 73/431; 250/281
[58] Field of Search .................. 73/23.37, 431; 250/281

[56] References Cited

U.S. PATENT DOCUMENTS

| | | | |
|---|---|---|---|
| 3,853,637 | 12/1974 | Gray et al. ................................. 148/13 |
| 3,922,349 | 11/1975 | Osborne et al. .............................. 426/2 |
| 5,313,061 | 5/1994 | Drew et al. ............................... 250/281 |
| 5,399,856 | 3/1995 | Sandridge et al. .................... 250/252.1 |
| 5,525,799 | 6/1996 | Andresen et al. ....................... 250/288 |
| 5,686,655 | 11/1997 | Itoi ........................................ 73/23.37 |

FOREIGN PATENT DOCUMENTS 8-327622  12/1996  Japan .

*Primary Examiner*—Michael Brock
*Assistant Examiner*—Jay L. Politzer
*Attorney, Agent, or Firm*—Armstrong, Westerman, Hattori, McLeland & Naughton

[57] ABSTRACT

A shield is disposed between a gas chromatograph unit and a mass spectrometer unit and, further, the space between the gas chromatograph unit and the space the shield and the mass spectrometer unit are ventilated by a ventilating fan or ventilating fans. Thus the change in the temperature of the mass spectrometer unit is suppressed within a small range, so that the accuracy of analysis is enhanced.

9 Claims, 2 Drawing Sheets

GAS CHROMATOGRAPH/MASS SPECTROMETER

The present invention relates to a gas chromatograph/mass spectrometer system (GC/MS).

BACKGROUND OF THE INVENTION

A detector of a gas chromatograph (GC) continuously measures a specific physical property of the gas effluent from the column and draws a chromatogram representing the change in the specific physical property. Constituents of a sample are measured qualitatively based on the time (retention time) and/or quantitatively based on the intensity (i.e. height or area) of each peak in the chromatogram.

A gas chromatograph/mass spectrometer (GC/MS), on the other hand, carries out a mass spectrometric analysis for each constituent of the sample separated by the column with a mass spectrometer (MS) and thus enables highly sensitive and accurate identification of each constituent.

Since, in many cases, a gas chromatograph requires temperature control of the column, the column is disposed in an oven. Thus the casing of a gas chromatograph unit is generally large enough to accommodate an oven. In a conventional gas chromatograph system that uses a normal detector, such as a thermal conductivity detector (TCD) or a hydrogen flame ionization detector (FID), the detector is typically mounted on the top of the casing of the gas chromatograph unit. Therefore, a sample inlet for introducing a sample into the column and a sample outlet for taking out the separated sample are arranged on the top of the casing of the gas chromatograph unit, and a sample inlet of the detector is connected with the sample outlet.

In a conventional gas chromatograph/mass spectrometer, on the other hand, a mass spectrometer unit is placed at the side of a gas chromatograph unit since the mass spectrometer unit occupies a larger space than the normal detectors do and has such an original configuration that it is not designed to be mounted on the gas chromatograph. Besides, if the sample gas effluent from the column of the gas chromatograph travels a large distance, the separated constituents may be diffused, resulting in a poor sharpness of the peak. Therefore, in the conventional gas chromatograph/mass spectrometer, the sample outlet of the gas chromatograph unit and the sample inlet of the mass spectrometer unit are provided in the side of the respective unit in order to make the distance between the outlet of the column and the inlet of the mass spectrometer unit as small as possible.

As described above, in a gas chromatograph system using a normal detector, the sample outlet is disposed in the top of the casing and the gas passage inside the system is formed accordingly. If, on the other hand, a gas chromatograph is to be used as a unit in a gas chromatograph/mass spectrometer, the sample outlet must be disposed in the side of the casing of the unit and the passage must be modified accordingly. Further, also the interface of the electrical system for the power supply, control signal and detection signal transmission, etc., must be modified accordingly. Such modifications prevent the standardization of the gas chromatograph (or gas chromatograph unit) and increase the production cost. In usage also, an additional plan area (table-top or floor space) is necessary for the mass spectrometer unit at a side of the casing of the gas chromatograph unit, whereas a normal detector does not require such an additional area because it is mounted on the top of the casing as described above. The irregular configuration of a conventional gas chromatograph system with a mass spectrometer unit thus prevents consistent arrangement of gas chromatograph units and reduces the efficiency of utilising space in conventionally narrow laboratories or the like.

In view of the above problems, the inventor proposed a gas chromatograph/mass spectrometer comprising a mass spectrometer unit having such a different structure that it can be mounted on the top of a gas chromatograph unit (see Publication No. H8-327622 of Japanese Unexamined Patent Application, or the corresponding U.S. Pat. No. 5,686,655 allowed on Apr. 15, 1997). By the above invention, it is no longer necessary to change the structure of the gas chromatograph unit depending on whether a normal detector or a mass spectrometer is used, so that the structure of the gas chromatograph unit can be standardized. Thus the production cost can be reduced and the plan area for installing the gas chromatograph/mass spectrometer can be reduced in size also.

In the event that the mass spectrometer unit is mounted on the gas chromatograph unit, however, the following problem must be considered.

The mass spectrometer is an apparatus constituted so precisely that, when a change in the temperature causes a thermal expansion of the mechanical components or a change in the property of the devices used in the electric circuit, etc., the operation of the mass spectrometer becomes unstable and a drift occurs in the result of the measurement. Therefore, it is generally recommended to suppress the change in the temperature of the mass spectrometer unit within a range of about ±5[°C.]. In view of this, some known gas chromatograph/mass spectrometers are provided with a temperature control system to maintain the temperature constant.

As explained above, the gas chromatograph unit includes an oven for heating the column, and the temperature of the column is changed within a range of about −40[°C.] to 450[°C.], depending on the analysis. Even though the oven is surrounded by a thermal insulation member, when the analysis is carried out with the column heated up to the maximum temperature, the top of the casing of the gas chromatograph unit becomes considerably hot and the temperature of the mass spectrometer mounted thereon rises up to several tens [°C.], which is too high to obtain a reliable measurement result.

SUMMARY OF THE INVENTION

In view of the above problem, the present invention proposes a gas chromatograph/mass spectrometer including:

a gas chromatograph unit including an oven for heating a gas chromatographic column;

a mass spectrometer unit mounted on the top of the gas chromatograph unit;

a shield disposed between the gas chromatograph unit and the mass spectrometer unit; and a ventilator for ventilating a space between the gas chromatograph unit and the shield and a space between the mass spectrometer and the shield.

In the above gas chromatograph/mass spectrometer the radiant heat generated from the gas chromatograph unit is prevented from reaching the mass spectrometer unit because of the shield disposed between the gas chromatograph unit and the mass spectrometer unit. Further, since the space between the gas chromatograph unit and the shield and the space between the mass spectrometer and the shield are ventilated by the ventilator, the transfer of heat from the gas chromatograph unit to the mass spectrometer unit by the conduction through or convection by the air is also prevented. Thus the change in the temperature of the mass spectrometer unit is suppressed, so that mass spectrometry can be carried out with high accuracy.

The shield need not be made of a thermal insulation material since the shield is primarily expected to screen the radiant heat, as described above. However, it is of course preferable to use thermal insulation material, whereby the amount of heat conducted through the air or component members for supporting the mass spectrometer unit on the gas chromatograph unit is reduced furthermore. Regarding the ventilation of the space between the gas chromatograph unit and the shield and the space between the mass spectrometer and the shield, each space may be provided with a ventilator, or, in some cases, both spaces may be ventilated by one ventilator by disposing the ventilator in an appropriate way.

The above description mainly relates to such a case that the column is heated by the oven and the gas chromatograph unit becomes hotter. It should be noted, however, that the present invention is also effective in such a case that the column is cooled by liquefied nitrogen or the like and the gas chromatograph unit becomes colder.

DETAILED DESCRIPTION OF PREFERRED EMBODIMENTS

Figure 1:
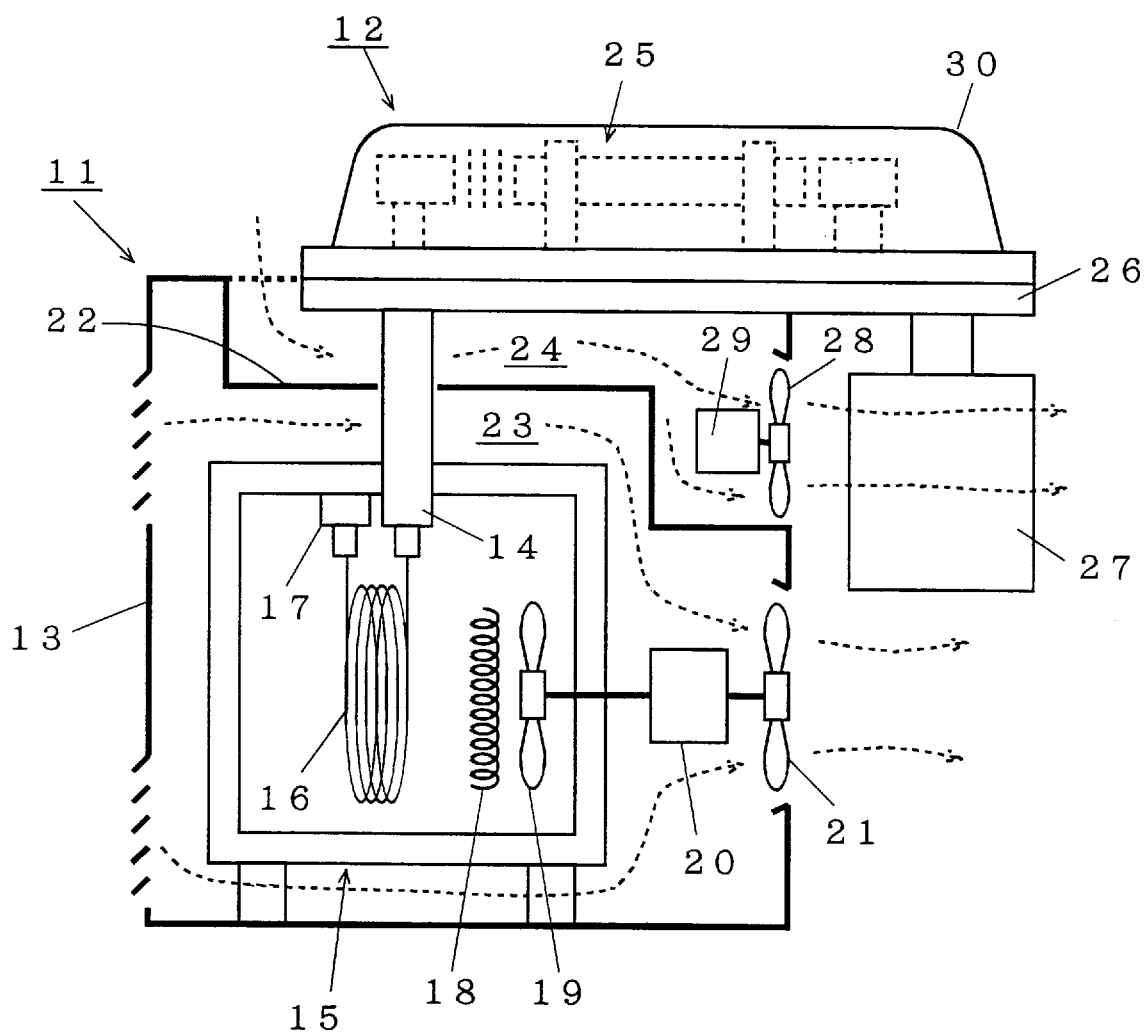
FIG. 1 is a vertical section of a gas chromatograph/mass spectrometer according to the present invention.

A gas chromatograph/mass spectrometer 10 embodying the present invention is described referring to FIG. 1. The gas chromatograph/mass spectrometer includes a gas chromatograph unit 11 and a mass spectrometer unit 12, where the mass spectrometer unit 12 is mounted on the top of a casing 13 of the gas chromatograph unit 11. A gas conduit 14 and an electrical cable (not shown) are provided for connecting the two units.

The gas chromatograph unit 11 includes an oven 15 in which a capillary column 16 is provided that is attachable to and detachable from the inside of the oven 15. One end of the capillary column 16 is connected to a sample inlet 17 and the other end is connected to the gas conduit 14. The sample inlet 17 is sticking up through the top of the casing 13 behind the gas conduit 14 (i.e. at the back side of the drawing paper, as it were).

In the oven 15, further, a heater 18 and a fan 19 connected to a control unit (not shown) are provided for controlling the temperature of the capillary column 16. The oven 15 is surrounded by a thermal insulation member and is disposed in the casing 13, leaving an adequate space between the oven 15 and the walls of the casing 13. The space is designed to be larger at the rear (i.e. the right side in FIG. 1) of the oven 15, and a first fan motor 20 is disposed there. The fan 19 in the oven 15 is fixed to one end of the rotation axis of the first fan motor 20, whereas a first ventilating fan 21 provided at the rear of the casing 13 is fixed to the other end of the rotation axis.

The mass spectrometer unit 12 includes an ion source, an ion lens, a quadrupole, an ion detector, etc. The assembly of the above members in the mass spectrometer unit 12 is called "a mass spectrometer assembly 25" hereinafter. All the members of the mass spectrometer assembly 25 are fixed to the top of a planer base plate 26 and are enclosed with a bath-tub shaped cover 30, which is air-tight. By placing the mass spectrometer assembly 25 on the base plate 26 as described above, the mass spectrometer unit 12 can be mounted on the top of the gas chromatograph unit 11. Further, the maintenance of the mass spectrometer assembly 25 can be facilitated by the above configuration since, when the cover 30 is removed, the mass spectrometer assembly 25 stands open and can be accessed freely from any direction. In addition, a vacuum pump 27, such as a turbo molecular pump, is connected with the mass spectrometer unit 12 to evacuate it.

As shown in FIG. 1, the mass spectrometer unit 12 is mounted on the top of the gas chromatograph unit 11 leaving a distance from the top plate 22 of the casing 13. In such a structure, the top plate 22 of the casing 13 functions as a shield between the oven 15 of the gas chromatograph unit 11 and the base plate 26 of the mass spectrometer unit 12. Besides, the top plate 22, or the shield 22, divides the space between the oven 15 and the base plate 26 into two spaces 23 and 24. The space 23 between the oven 15 and the shield 22 is ventilated by the first ventilating fan 21, and the space 24 between the shield 22 and the base plate 26 is ventilated by a second ventilating fan 28 driven by a second fan motor 29.

In the gas chromatograph/mass spectrometer 10 of the present embodiment, both of the fan 19 in the oven 15 and the first ventilating fan 21 are driven by one and the same motor, i.e. the first fan motor 20, so that the configuration is simplified and the production cost is reduced. Furthermore, the second ventilating fan 28 may be preferably driven by the first fan motor 20 by means of a transmission mechanism, such as a belt-pulley mechanism, instead of providing the second fan motor 29 used exclusively for driving the second ventilating fan 28. In another preferable case, as shown in FIG. 2, the casing 13 is designed so that both of the spaces 23 and 24 lead to an opening 32 provided at the rear of the casing 13 and a ventilating fan 31 driven by the first fan motor 20 is disposed in the opening 32 to ventilate both spaces 23 and 24, whereby the configuration is simplified and thus the production cost is reduced furthermore.

Figure 2:
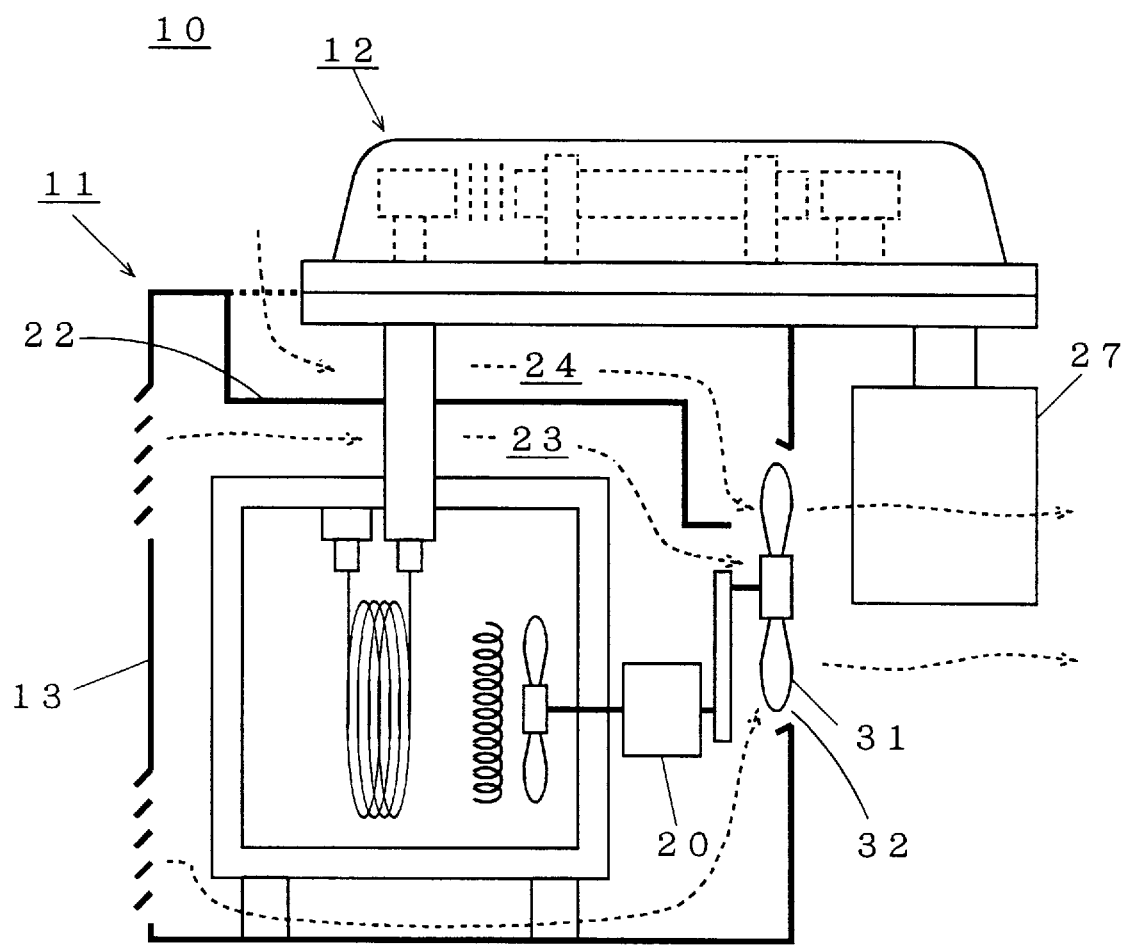
FIG. 2 is a vertical section of another gas chromatograph/mass spectrometer according to the present invention.

In addition, the second ventilating fan 28 in FIG. 1 or the ventilating fan 31 in FIG. 2 also functions as a cooler of the vacuum pump 27 during the ventilating operation, which is also advantageous in respect of the simplification of the configuration and the reduction of the cost compared to some conventional gas chromatograph/mass spectrometers which include a fan for cooling the vacuum pump.

As described above, in the gas chromatograph/mass spectrometer 10 of the present embodiment, the shield 22 disposed between the oven 15 of the gas chromatograph 11 and the base plate 26 of the mass spectrometer unit 12 prevents the radiant heat from the oven 15 from reaching the mass spectrometer unit 12. Further, since the spaces 23 and 24 at both sides of the shield 22 are ventilated, the transfer of the heat from the oven 15 to the mass spectrometer unit 12 by the conduction through or convection by the air is also prevented. Owing to such a configuration, the fluctuation in the temperature of the mass spectrometer unit 12 is suppressed within a small range of about ±2[°C.] even when the temperature of the capillary column 16 is varied within a wide range from −40[°C.] to 450[°C.], so that the accuracy of the analysis is enhanced.

The mass spectrometer unit 12 is usually equipped with a control circuit or a driving circuit including a high voltage generating circuit. The high voltage generating circuit generates the heat during the operation, whereby the temperature of the circuit rises. The temperature of the circuit, however, must be maintained as stable as possible since the correct processing of the control signal and detection signal requires a precise voltage control and the stability of the circuits, whereas the change in the temperature may cause an error of the control signal or a drift of the detection signal. In view of this, a control circuit or a driving circuit of the mass spectrometer unit 12 may be preferably disposed at a location where the flow of air is generated, for example in the space 24 between the shield 22 and the base plate 26, whereby the temperature of the circuit can be stabilized, so that the stability of control and the accuracy of the analysis can be enhanced.

Finally, it should be appreciated that the above embodiment is just illustrative and can be modified within the true spirit and scope of the appended claims.

What is claimed is:

1. A gas chromatograph/mass spectrometer comprising:
   a gas chromatograph unit including an oven for heating a gas chromatographic column;
   a mass spectrometer unit mounted on a top of the gas chromatograph unit;
   a shield disposed between the gas chromatograph unit and the mass spectrometer unit; and
   ventilating means for ventilating a space between the gas chromatograph unit and the shield and a space between the mass spectrometer and the shield.

2. The gas chromatograph/mass spectrometer according to claim 1, wherein the shield is made of a thermal insulating material.

3. The gas chromatograph/mass spectrometer according to claim 1, wherein the ventilating means comprises a ventilating fan for ventilating both of the space between the gas chromatograph unit and the shield and the space between the mass spectrometer and the shield.

4. The gas chromatograph/mass spectrometer according to claim 2, wherein the ventilating means comprises a ventilating fan for ventilating both of the spaces between the gas chromatograph unit and the shield and the space between the mass spectrometer and the shield.

5. The gas chromatograph/mass spectrometer according to claim 1, wherein part of an electrical system of the mass spectrometer unit including a high voltage generating circuit is disposed in a space where a flow of air generated by the ventilating means is supplied.

6. The gas chromatograph/mass spectrometer according to claim 2, wherein part of an electrical system of the mass spectrometer unit including a high voltage generating circuit is disposed in a space where a flow of air generated by the ventilating means is supplied.

7. The gas chromatograph/mass spectrometer according to claim 3, wherein part of an electrical system of the mass spectrometer unit including a high voltage generating circuit is disposed in a space where a flow of air generated by the ventilating means is supplied.

8. The gas chromatograph/mass spectrometer according to claim 4, wherein part of an electrical system of the mass spectrometer unit including a high voltage generating circuit is disposed in a space where a flow of air generated by the ventilating means is supplied.

9. The gas chromatograph/mass spectrometer according to one of claims 1–8, wherein evacuating means for evacuating the mass spectrometer unit is disposed in a space where a flow of air generated by the ventilating means is supplied.

* * * * *